United States Patent
Lorio et al.

(10) Patent No.: US 9,131,969 B2
(45) Date of Patent: Sep. 15, 2015

(54) SPINAL PLATE AND METHOD FOR USING SAME

(76) Inventors: Morgan Packard Lorio, Bristol, TN (US); Rocky Wayne Renfro, Kingsport, TN (US)

(*) Notice: Subject to any disclaimer, the term of this patent is extended or adjusted under 35 U.S.C. 154(b) by 186 days.

(21) Appl. No.: 13/538,824

(22) Filed: Jun. 29, 2012

(65) Prior Publication Data

US 2013/0006309 A1    Jan. 3, 2013

Related U.S. Application Data

(60) Provisional application No. 61/503,351, filed on Jun. 30, 2011.

(51) Int. Cl.
*A61B 17/80* (2006.01)
*A61B 17/70* (2006.01)
*A61B 17/86* (2006.01)

(52) U.S. Cl.
CPC ......... *A61B 17/8042* (2013.01); *A61B 17/7059* (2013.01); *A61B 17/8033* (2013.01); *A61B 17/8605* (2013.01)

(58) Field of Classification Search
CPC .................................. A61B 17/8033
USPC .................... 606/70, 71, 281–299
See application file for complete search history.

(56) References Cited

U.S. PATENT DOCUMENTS

| | | | |
|---|---|---|---|
| 5,180,381 A | 1/1993 | Aust et al. | |
| 5,364,399 A | 11/1994 | Lowery et al. | |
| 5,601,553 A | 2/1997 | Trebing et al. | |
| 5,607,426 A | 3/1997 | Ralph et al. | |
| 5,904,684 A | 5/1999 | Rooks | |
| 6,139,550 A | 10/2000 | Michelson | |
| 6,328,738 B1 | 12/2001 | Suddaby | |
| 6,361,537 B1 | 3/2002 | Anderson | |
| 6,740,088 B1 * | 5/2004 | Kozak et al. | 606/286 |
| 6,786,909 B1 | 9/2004 | Dransfeld et al. | |
| 6,969,390 B2 | 11/2005 | Michelson | |
| 6,989,012 B2 | 1/2006 | LeHuec et al. | |
| 7,137,984 B2 | 11/2006 | Michelson | |

(Continued)

FOREIGN PATENT DOCUMENTS

WO    WO 2006/113353    10/2006

OTHER PUBLICATIONS

International Search Report and Written Opinion in PCT Application No. PCT/US2012/045062 dated Jan. 2, 2013 in 16 pages.

(Continued)

*Primary Examiner* — Andrew Yang
(74) *Attorney, Agent, or Firm* — Michael R. Shevlin

(57) ABSTRACT

A spinal plate for installation on one or more vertebrae. The spinal plate can be an asymmetrical cervical plate. The cervical plate can have a thicker side, a thinner side, one or more threaded fastener holes, and one or more locking fastener holes. The shape of the cervical plate can match the shape of a vertebra to facilitate installation, thus, the thickness of both the thicker and thinner sides, and shape of the cervical plate between the thicker side and the thinner side can match the shape of a vertebra. The cervical plate can include locking features that secure one or more locking fasteners in the one or more locking fastener holes, and thereby secure one or more threaded fasteners in the one or more threaded fastener holes.

29 Claims, 6 Drawing Sheets

(56) References Cited

U.S. PATENT DOCUMENTS

| | | | |
|---|---|---|---|
| 7,288,095 B2 * | 10/2007 | Baynham et al. | 606/288 |
| 7,468,069 B2 * | 12/2008 | Baynham et al. | 606/296 |
| 7,635,381 B2 | 12/2009 | Orbay | |
| 7,662,174 B2 | 2/2010 | Doubler et al. | |
| 7,670,360 B2 | 3/2010 | Catbagan et al. | |
| 7,699,880 B2 | 4/2010 | Orbay et al. | |
| 7,704,255 B2 | 4/2010 | Michelson | |
| 7,749,257 B2 | 7/2010 | Medoff | |
| 7,833,226 B2 | 11/2010 | Grabowski et al. | |
| 7,862,597 B2 | 1/2011 | Gause et al. | |
| 7,875,062 B2 | 1/2011 | Lindemann et al. | |
| 7,955,362 B2 | 6/2011 | Erickson et al. | |
| 8,617,222 B2 * | 12/2013 | Shipp et al. | 606/289 |
| 2004/0210221 A1 | 10/2004 | Kozak et al. | |
| 2005/0096657 A1 | 5/2005 | Autericque et al. | |
| 2005/0187551 A1 | 8/2005 | Orbay et al. | |
| 2005/0234455 A1 | 10/2005 | Binder et al. | |
| 2006/0122603 A1 | 6/2006 | Kolb | |
| 2006/0195085 A1 * | 8/2006 | Happonen et al. | 606/61 |
| 2006/0212035 A1 | 9/2006 | Wotton, III | |
| 2006/0247632 A1 | 11/2006 | Winslow et al. | |
| 2008/0154310 A1 | 6/2008 | White et al. | |
| 2008/0275562 A1 * | 11/2008 | Clifford et al. | 623/20.21 |
| 2009/0024171 A1 | 1/2009 | Leone | |
| 2009/0118764 A1 | 5/2009 | Vaughan | |
| 2009/0163959 A1 | 6/2009 | Deeter et al. | |
| 2010/0082068 A1 | 4/2010 | Graham | |
| 2010/0198266 A1 | 8/2010 | Nassab | |
| 2010/0256687 A1 | 10/2010 | Neufeld et al. | |
| 2011/0004252 A1 | 1/2011 | Velikov | |
| 2011/0306977 A1 * | 12/2011 | Michel et al. | 606/71 |
| 2012/0065686 A1 | 3/2012 | Black et al. | |
| 2012/0265203 A1 | 10/2012 | Angelucci et al. | |
| 2012/0277803 A1 * | 11/2012 | Remesh et al. | 606/289 |

OTHER PUBLICATIONS

Invitation to Pay Additional Fees and Where Applicable, Protest Fee in PCT Application No. PCT/US2012/045062 dated Oct. 30, 2012 in 9 pages.

* cited by examiner

SPINAL PLATE AND METHOD FOR USING SAME

CROSS-REFERENCE TO RELATED APPLICATIONS

This application claims the benefit of U.S. Provisional Patent Application No. 61/503,351, filed Jun. 30, 2011, the entirety of which is incorporated by reference herein.

This application is related to Applicant's co-pending PCT application entitled SPINAL PLATE AND METHOD FOR USING SAME, International Application No. PCT/US2012/045062, filed Jun. 29, 2012, the disclosure of which is hereby incorporated by reference in its entirety herein.

BACKGROUND OF THE INVENTION

1. Field of the Invention

This application relates to the field of spinal plates.

2. Description of the Related Art

Surgeons use a variety of devices and techniques to provide treatments to patients. In some operations, medical devices are used to connect, stabilize, and/or secure one or more bones, bone pieces, or tissue pieces. Similar techniques and devices are used in spinal surgery, and particularly in spinal fusion surgery. In some of these procedures, a plate can be affixed to one or several vertebrae. These plates are typically symmetrical and are typically affixed centered on the spine.

While such designs offer many advantages, they also can be difficult to insert. These difficulties limit the number doctors who use such techniques in surgery, and thereby negatively impact patients needing treatment. Further, difficulties in placement of these existing plates can increase a patient's risk of infection and increase a patient's risks of negative surgical outcomes. In light of these problems, additional plate designs are desired.

SUMMARY OF THE INVENTION

Certain embodiments of the present application relate to a spinal plate and methods of manufacture and use of the same. For example, certain embodiments relate to a cervical plate, and more particularly, to an offset cervical plate for placement along an anterior surface of the cervical spine.

In one embodiment, the spinal plate has an asymmetrical configuration for off-center affixation to the vertebral spine, wherein bone engaging fasteners extending through holes in the plate are vertically aligned to one side of the center of the vertebral spine. In one embodiment, the spinal plate has a unique geometry for positioning in and conforming to the valley between the cervical body and the cervical anterior tubercle.

In one embodiment, the spinal plate includes holes for receiving bone engaging fasteners and locking fasteners used to secure the bone engaging fasteners. The locking fasteners may extend through the spinal plate at an acute angle relative to the bone engaging fasteners. In some aspects, the locking fasteners may also engage bone. In some aspects, the locking fasteners are at least partially threaded into a threaded hole in the spinal plate to engage and prevent movement of the bone engaging fasteners. In some aspects, a locking mechanism such as a spring-loaded ball is configured to interact with notches in the head of the locking fasteners to prevent rotational movement of the locking fastener and thereby, and in connection with the threads, also prevent longitudinal translation of the locking fasteners.

In one embodiment, a locking mechanism for use in the spine can include a spring loaded ball that interacts with the head of a fastener. The fastener may be a bone engaging fastener for use with a spinal plate as described herein, or may be any other type of fastener used in a spinal or other medical application. In one embodiment, a medical device having a locking mechanism with a resilient securing feature that interacts with the head of a fastener for use in a patient's body is provided. In one embodiment, the locking mechanism may comprise a locking screw that is insertable into the spine or other part of a patient's body.

In one embodiment, any of the above disclosed components is included in a kit with at least one of a surgical tool, a medical device, medication, or an implantable item used in conjunction with the delivery of the component(s) or treatment of the patient.

In one embodiment, a method is provided for affixing a medical device to a patient's body. In one embodiment, a method of implanting a spinal plate is provided. In one embodiment, a method is provided including affixing an asymmetrical spinal plate in an off-center configuration relative to the vertebral spine, and delivering fasteners through the plate and into adjacent vertebral bodies. These fasteners can be vertically aligned to one side of the center of the vertebral spine. In one embodiment, the spinal plate may have a unique geometry to be positioned in the valley between the cervical body and the cervical anterior tubercle.

In one embodiment, a method of implanting a spinal plate includes delivering bone engaging fasteners through the plate into adjacent vertebral bodies, and using locking fasteners to secure the bone engaging fasteners. The locking fasteners may extend at an acute angle relative to the threaded fasteners. In some aspects, the locking fasteners may also engage bone. In some aspects, the locking fasteners can be least partially threaded into a threaded hole in the spinal plate to engage and prevent movement of the bone engaging fasteners. In some aspects, a locking mechanism such as a spring-loaded ball can be configured to interact with notches in the head of the locking fasteners to prevent rotational movement of the locking fastener and thereby, and in connection with the threads, also prevent longitudinal translation of the locking fasteners.

According to one aspect, a spinal plate apparatus is provided. In one embodiment, the spinal plate apparatus can include, for example, a spinal plate that can include, for example, an upper surface, a lower surface, a first end and a second end defining a length therebetween that spans two or more adjacent vertebral bodies, a first side and a second opposing side. In one embodiment, the spinal plate apparatus can include, for example, at least two holes extending through the upper and lower surfaces, which at least two holes are positioned closer to the second side than to the first side and the at least two holes are angled toward the first side of the spinal plate.

According to one embodiment, the spinal plate apparatus can further include at least two bone engaging fasteners that each extend through a corresponding hole at an oblique angle extending from the second side toward the first side of the plate. In one embodiment, the at least two holes can include a first hole and a second hole, and in one embodiment, the at least two holes can include a third hole located proximate to the first hole and a fourth hole located proximate to the second hole. In one embodiment, the spinal plate apparatus can include locking fasteners that are received in the third and fourth holes to secure the bone engaging fasteners to the spinal plate.

According to one embodiment of the spinal plate apparatus, a portion of the third hole and a portion of the fourth hole can be threaded. In one embodiment of the spinal plate apparatus, the third hole can be positioned at an acute angle relative to the first hole and the fourth hole can be positioned at an acute angled relative to the second hole.

According to one embodiment the spinal plate apparatus, the distance between the upper surface and the lower surface defines a thickness, and in some embodiments of the spinal plate apparatus, the thickness at the second side can be greater than the thickness at the first side. In one embodiment of the spinal plate apparatus, the lower surface of the plate can be concave.

According to one aspect, a spinal plate apparatus is provided. In one embodiment, the spinal plate apparatus can include, for example, a spinal plate having an asymmetrical configuration that allows for off-center affixation to the vertebral spine.

According to one embodiment of the spinal plate apparatus, the spinal plate can include, for example, an upper surface, a lower surface, a thickness between the upper and lower surfaces, a first end and a second end defining a length therebetween configured to span two or more adjacent vertebral bodies, a first side and a second opposing side. In one embodiment of the spinal plate apparatus, the asymmetrical configuration includes a variation in the thickness of the spinal plate that can, for example, correspond to the geometry of a cervical vertebra. In one embodiment of the spinal plate apparatus, the thickness of the second side can be greater than the thickness of the first side. In one embodiment of the spinal plate apparatus, the lower surface can be concave. In one embodiment of the spinal plate apparatus, the spinal plate includes at least one bone engaging fastener hole extending through the upper and the lower surfaces.

According to one embodiment of the spinal plate apparatus, the asymmetrical configuration can include at least two holes that can receive fasteners extending through the upper and lower surfaces. These at least two holes can be, for example, positioned closer to the second side than to the first side, and in one embodiment of the spinal plate apparatus, the at least two holes are angled toward the first side of the spinal plate.

According to one embodiment, the spinal plate apparatus further includes at least one bone engaging fastener that can be delivered through the corresponding bone engaging fastener hole in the spinal plate, which can, in some embodiments, extend through the corresponding bone engaging hole in the spinal plate at an oblique angle extending from the second side toward the first side of the plate. In one embodiment, the spinal plate apparatus can further include, for example, bone engaging fasteners that each extend through a corresponding hole in the spinal plate at an oblique angle extending from the second side toward the first side of the plate.

According to one embodiment, the spinal plate apparatus further includes at least one locking fastener hole located proximate to the corresponding bone engaging fastener hole. In one embodiment, the spinal plate apparatus can further include at least one locking fastener that can be received in a corresponding locking fastener hole to secure at least one bone engaging fastener to the spinal plate. In one embodiment of the spinal plate apparatus, a portion of the locking fastener hole is threaded. In one embodiment of the spinal plate apparatus the locking fastener hole can be positioned at an acute angle relative to a corresponding bone engaging fastener hole. In one embodiment, the spinal plate apparatus can further include a locking feature that can engage with a locking fastener when the locking fastener is delivered through the locking fastener hole, wherein the locking feature can secure the locking fastener and thereby secure a corresponding bone engaging fastener when the bone engaging fastener is delivered through the bone engaging fastener hole. In one embodiment of the spinal plate apparatus, the locking feature can engage with a head of the locking fastener.

According to one embodiment of the spinal plate apparatus, the head of the locking fastener can include a plurality of notches. In one embodiment of the spinal plate apparatus, the locking feature engages with the plurality of notches of the head of the locking fastener. In one embodiment of the spinal plate apparatus, the bone engaging fastener hole can be positioned such that a head of the bone engaging fastener can be partially disposed between the spinal plate and a head of the locking fastener when the bone engaging fastener is inserted into the bone engaging fastener hole and the locking fastener is inserted into the locking fastener hole. In one embodiment of the spinal plate apparatus, the locking feature can include a spring-loaded detent ball.

According to one aspect, a spinal plate apparatus is provided. According to one embodiment, the spinal plate apparatus can include, for example, a spinal plate having at least one bone engaging fastener hole, and at least one locking fastener hole positioned adjacent to the bone engaging fastener hole. In one embodiment, the spinal plate apparatus can include, at least one bone engaging fastener that can be delivered through the at least one bone engaging fastener hole, at least one locking fastener that can be delivered through the locking fastener hole, and a locking feature that can engage with the locking fastener when the locking fastener is delivered through the locking fastener hole. In one embodiment, the locking feature can secure the locking fastener and thereby secure the bone engaging fastener when the bone engaging fastener is delivered through the bone engaging fastener hole.

According to one embodiment of the spinal plate apparatus, the at least one bone engaging fastener can be a threaded fastener. In one embodiment of the spinal plate apparatus, the at least one bone engaging fastener hole defines an axis through which the bone engaging fastener can be delivered that can be at an acute angle with an axis defined by the at least one locking fastener hole through which the locking fastener can be delivered. In one embodiment of the spinal plate apparatus, the at least one bone engaging fastener hole can define an axis through which the bone engaging fastener can be delivered that can be at an acute angle with a lower surface of the spinal plate, and the at least one locking fastener hole defines an axis through which the locking fastener can be delivered that can be substantially perpendicular to the lower surface of the spinal plate.

According to one embodiment, the spinal plate apparatus can include, for example, at least two bone engaging fastener holes and at least two locking fastener holes located proximate to corresponding bone engaging fastener holes. In one embodiment of the spinal plate apparatus, a portion of the at least one locking fastener hole can be threaded.

According to one embodiment of the spinal plate apparatus, the bone engaging fastener can include a head and a shaft and the locking fastener can include a head and a shaft, and in one embodiment of the spinal plate apparatus, the locking feature can engage with the head of the locking fastener. The head of the locking fastener can, in one embodiment of the spinal plate apparatus, include a plurality of notches, and in one embodiment of the spinal plate apparatus, the locking feature engages with the plurality of notches of the head of the locking fastener. In one embodiment of the spinal plate apparatus, the locking feature can be a spring-loaded detent ball.

According to one embodiment of the spinal plate apparatus, the at least one bone engaging fastener hole can be positioned such that the head of the bone engaging fastener can be partially disposed between the spinal plate and the head of the locking fastener when the bone engaging fastener is inserted into the bone engaging fastener hole and the locking fastener is inserted into the locking fastener hole.

According to one aspect, a method of implanting a spinal plate is provided. In one embodiment, this can include, for example, affixing an asymmetrical spinal plate in an off-center configuration relative to the vertebral spine, and delivering fasteners through the plate and into adjacent vertebral bodies. In one embodiment, the fasteners can be positioned to one side of the center of the vertebral spine.

According to one embodiment of the method of implanting a spinal plate, the fasteners once delivered can be vertically aligned to one side of the center of the vertebral spine. In one embodiment of the method of implanting a spinal plate, all of the fasteners delivered through the plate and into adjacent vertebral bodies can be positioned to one side of the center of the vertebral spine. In one embodiment of the method of implanting a spinal plate, the spinal plate can be positioned in the valley between the cervical body and the cervical anterior tubercle.

According to one embodiment of the method of implanting a spinal plate, the spinal plate can have a thinner side and a thicker side, and the thicker side can be, for example, positioned in the valley between the cervical body and the cervical anterior tubercle and the thinner side can extend toward and over the centerline of the vertebrae. In one embodiment of the method of implanting a spinal plate, the spinal plate has a thinner side and a thicker side, and the thicker side can be located on the anatomical left side of the vertebrae, and in some embodiments, the thicker side can be located on the anatomical right side of the vertebrae.

According to one embodiment of the method of implanting a spinal plate, the fasteners can be delivered through openings in the spinal plate from a position to one side of the center of the vertebral spine in a direction toward the center of the vertebral spine. In one embodiment of the method of implanting a spinal plate, the spinal plate scan pan at least two vertebral bodies and/or at least three vertebral bodies, and in one embodiment of the method of implanting a spinal plate, the spinal plate can be affixed to cervical vertebrae.

According to one embodiment of the method of implanting a spinal plate, delivering the fasteners can include delivering bone engaging fasteners through the plate into adjacent vertebral bodies, and using locking fasteners to engage the bone engaging fasteners. In one embodiment of the method of implanting a spinal plate, the locking fasteners can extend at an acute angle relative to the bone engaging fasteners. In one embodiment of the method of implanting a spinal plate, the locking fasteners can engage bone, and/or can be at least partially threaded into a threaded hole in the spinal plate to engage and prevent movement of the bone engaging fasteners. In one embodiment of the method of implanting a spinal plate, a locking mechanism is configured to interact with notches in heads of the locking fasteners to prevent rotational movement of the locking fastener and thereby also prevent longitudinal translation of the locking fasteners.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the devices and/or processes and/or other subject matter described herein will become apparent in the teaching set forth herein. The summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

DETAILED DESCRIPTION OF THE PREFERRED EMBODIMENTS

Some embodiments relate to a spinal plate that can be configured for affixation to one or several vertebrae. In some embodiments, the spinal plate can comprise an asymmetrical plate configured for offset attachment to one or several vertebrae. In some embodiments, this offset can be to one side of the centerline of the one or several vertebrae. Advantageously, such an asymmetrical spinal plate can be configured to match vertebral anatomy when the spinal plate is placed in an offset position. Further, the use of the offset position can advantageously facilitate placement of the plate, can minimize interference with other anatomical structures proximate to the plate, and can decrease the likelihood of adverse outcomes of the plate installation.

Some embodiments relate to a locking system. In some embodiments, the locking system can be configured to secure a first fastener after it has been inserted into and/or through the spinal plate. In some embodiments, the first fastener can be secured by positioning a locking fastener at least partially above the first fastener, such that a portion of the first fastener is secured between the spinal plate and the locking fastener. In some embodiments, the locking fastener can be secured in place by a locking feature that can secure the locking fastener. Advantageously, the use of a locking fastener to secure the first fastener can prevent the first fastener becoming loose and or retracting. Further, the use of a separate locking fastener can facilitate the use of a wide range of first fasteners as the first fastener does not require any special features for locking.

The Spinal Plate

Figure 1:
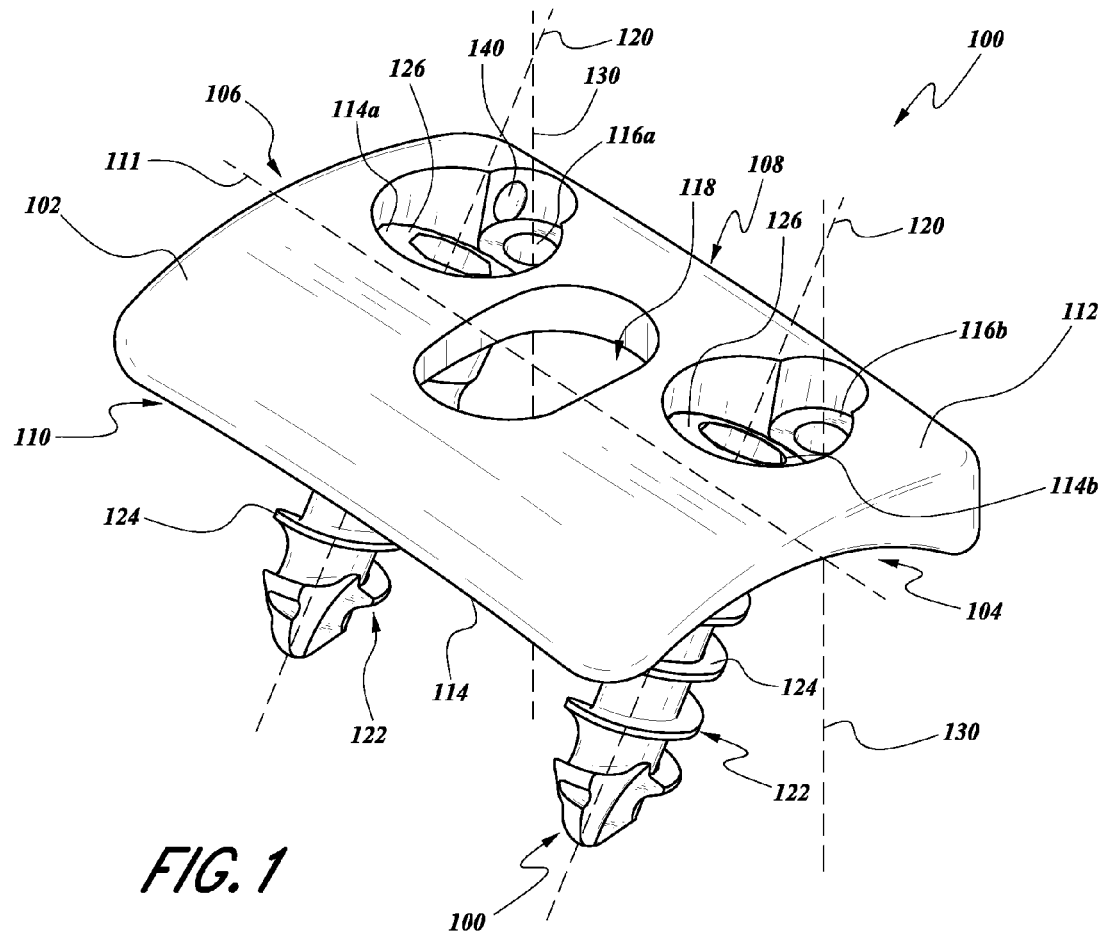
FIG. 1 is a perspective view of one embodiment of a spinal plate.
Figure 2:
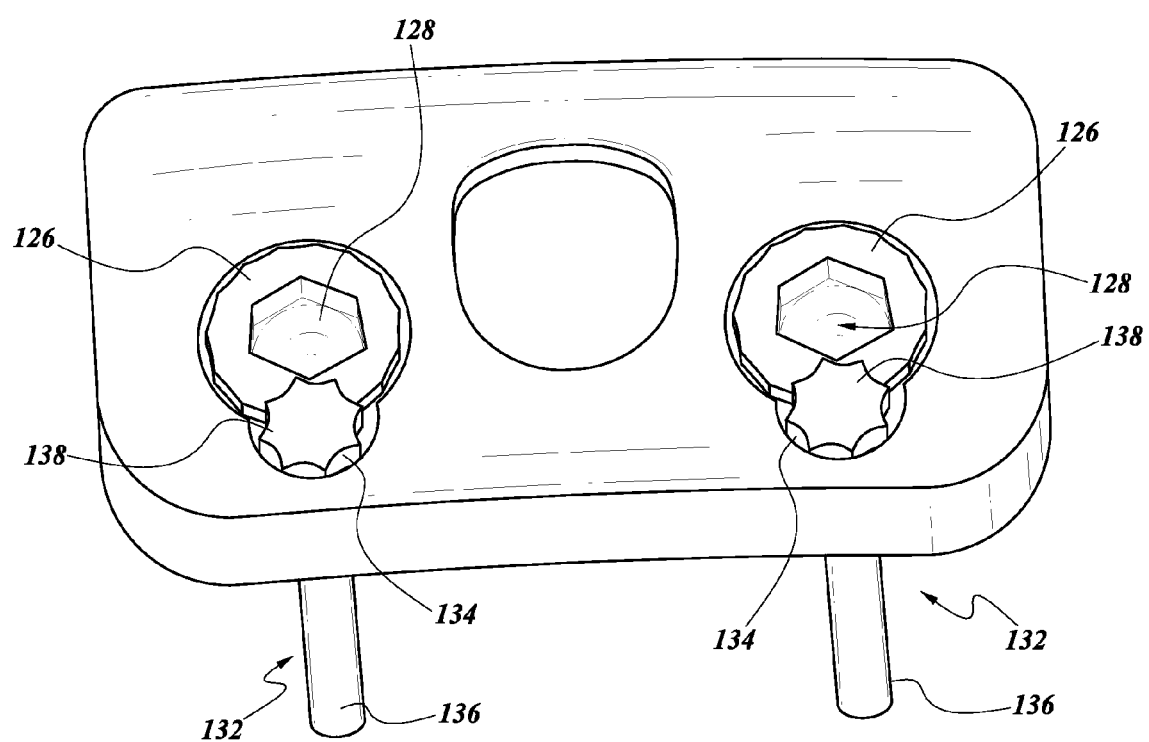
FIG. 2 is a top view of one embodiment of a spinal plate.

As shown in FIG. 1 and FIG. 2, a spinal plate, preferably a cervical plate 100, is provided. The cervical plate 100 comprises a body 102 having a roughly rectangular outline defined by a first end 104, a second end 106, a thicker side 108, and a thinner side 110. In some embodiments, a midline axis 111 can be located mid-way between the thicker side 108 and the thinner side 110.

The cervical plate 100 can further include an upper surface 112 and a lower surface 114. In some embodiments, the distance between the upper surface 112 and the lower surface 114 can define a thickness. The upper surface 112 of the cervical plate 100 is generally convex, and the lower surface 114 of the cervical plate 100 is generally concave. Advantageously, this shaping of the cervical plate can, in some embodiments, facilitate placement of the cervical plate against the anterior surface of a patient's cervical spine.

As also shown in FIGS. 1 and 2, one embodiment of a cervical plate 100 includes four paired holes 114a, 114b, 116a, 116b for receiving fasteners and a central opening 118 for providing access or visualization to areas underneath the body 102. Two of the fastener holes, threaded fastener holes and/or bone engaging fastener holes 114a, 114b can be configured for receiving a threaded fastener and/or a bone engaging fastener, and two of the fastener holes, the locking fastener holes 116a, 116b can be configured for receiving and securing locking fasteners. The holes 114a, 114b, 116a, 116b are located relatively more proximate to the thicker side 108 of the body 102, with each of the threaded fastener holes 114a, 114b positioned near one of the corners of the thicker side 108 of the cervical plate 100. Similarly, each of the locking fastener holes 116a, 116b is positioned in proximity to one of the corners on the thicker side 108 of the cervical plate 100 and adjacent to one of the threaded fastener holes 114a, 114b. The holes 114a, 114b, 116a, 116b are paired so that each threaded fastener hole 114a, 114b is paired with one of the locking fasteners holes 116a, 116bs. As illustrated, each locking fasteners hole 116a, 116b is positioned between the threaded fastener hole 114a, 114b and the thicker side 108 of the cervical plate 100.

Each of the threaded fastener holes 114a, 114b defines an axis 120 along which the threaded fasteners may be inserted in order to be delivered into bone. These threaded fastener hole axes 120 may be angled toward the thinner side 110 of the cervical plate 100 such that the threaded fasteners 122 extend toward the thinner side 110 of the cervical plate 100 when they are inserted, and form an acute angle with the lower surface 114 of the cervical plate 100. In some embodiments, this angle can be, for example, between 10 degrees and 90 degrees, between 30 degrees and 70 degrees, approximately 60 degrees, and/or any other or intermediate angle. Thus, when the body 102 is positioned on a patient's vertebrae, the threaded fasteners 122 may be delivered into a patient's vertebrae at an oblique angle starting from the thicker side 108 and extending toward the thinner side 110.

The threaded fasteners 122 may include a threaded shaft 124 and an enlarged head 126 with an internal hex opening 128 for engagement with a suitable delivery instrument. The enlarged head 126 is configured to engage an internal surface of a threaded fastener hole 114a, 114b to prevent the threaded fasteners 122 from passing beyond the lower surface 114 of the cervical plate 100 when the threaded fastener 122 is inserted into the cervical plate 100.

Additionally, each of the locking fasteners holes 116a, 116b also defines an axis 130 through which the locking fasteners 132 may be delivered. The axes 130 of the locking fasteners holes 116a, 116b may be non-parallel and may, for example, form an acute angle with respect to the axes 120 of the threaded fastener holes 114a, 114b. In some embodiments, for example, the locking fasteners 132 may be inserted substantially perpendicular to the lower surface 114 of the cervical plate 100. In some embodiments, each of the locking fasteners holes 116a, 116b may be threaded, non-threaded, or partially threaded.

In some embodiments, the locking fasteners 132 can comprise a length such that the locking fasteners 132 do not extend beyond the cervical plate 100 after insertion into the cervical plate 100, and in some embodiments, the locking fasteners 132 comprise a length such that the locking fasteners 132 extend beyond the cervical plate 100 after insertion into the cervical plate 100. The locking fasteners 132 illustrated in FIG. 2 comprise a length and configuration such that the locking fasteners 132 extend beyond the cervical plate 100 and into a patent's bone after they are inserted into the cervical plate 100. The locking fasteners 132 may have a threaded, unthreaded, or partially threaded shaft.

As illustrated in FIG. 1, the locking fasteners holes 116a, 116b may have an upper portion with a relatively larger opening, and a lower portion having a relatively smaller opening. The locking fasteners 132 may have enlarged heads 134 that are positioned in the upper portion of the locking fasteners holes 116a, 116b, with downwardly extending shafts 136 that extend into the smaller opening of the lower portion (and optionally into bone). In some embodiments, the enlarged head 134 can include features configured for interaction with locking features of the cervical plate 100 (described below), such as at least one notch, at least one groove, or at least one depression. In some embodiments, these locking fasteners 132 may have a partially threaded shaft with an enlarged head 134 with a hexalobular internal driving feature (Torx™ drive) and a plurality of notches 138 extending around an outer circumference of the enlarged head 134. These notches 138 may engage the detent ball as described below. In an alternative embodiment, the locking fasteners 132 may have a shorter length that does not extend past the lower surface 114 of the cervical plate 100, such that the locking fasteners 132 only serve to secure the threaded fastener to the body 102.

The locking plate can additionally include features for securing the locking fasteners 132, and thereby the threaded fastener 122, after the threaded fasteners 122 have been inserted into their holes 114a, 114b. These features can include, for example, a spring-loaded detent ball 140, that can be configured to interact with or apply a force to features of the enlarged head 134 of the locking fastener 132 to secure the locking fastener 132 in the locking fastener hole 116a, 116b. In some embodiments, these features can interact with features of the locking fastener 132 to prohibit movement of the locking fastener 131, including, rotational or translational movements. In one embodiment, in which the locking fastener 132 has a partially threaded shaft 136, at least one locking feature can interact with at least one of a plurality of notches 138 extending around an enlarged head 134 of the locking fastener 132 to prevent rotation of the locking fastener 132, and thereby, and in connection with engaged threads of the locking fastener 132, also preventing longitudinal translation of the locking fastener 132.

As seen in FIG. 2, the enlarged head 134 of the locking fastener 132, when inserted, is positioned on top of the enlarged head 126 of the threaded fastener 122. In such a position, the enlarged head 126 of the threaded fastener 122 is positioned between the cervical plate 100 and the enlarged head 134 of the locking fastener 132. This positioning secures the threaded fasteners 122 as long as the locking fastener 132 maintains its position. Thus, by securing the locking fastener 132, the threaded fastener 122 is likewise secured.

Figure 3:
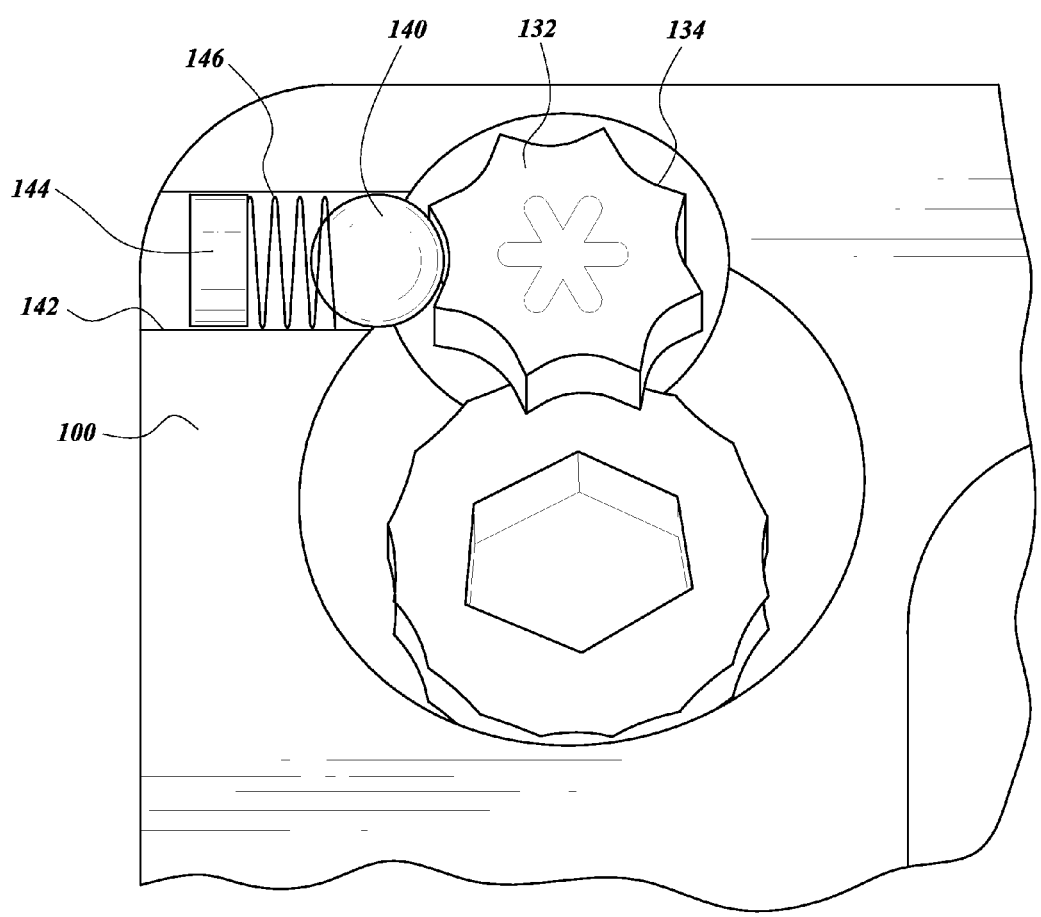
FIG. 3 is a close-up cut-away view of a locking mechanism of a spinal plate.

A cervical plate 100 can employ a variety of configurations for inclusion of a spring-loaded detent ball 140. As shown in FIG. 3, a cervical plate 100 can include a hole 142 configured for receiving a spring-loaded detent ball 140. The hole 142 can be located such that the hole 142 terminates proximate to the upper portion of one or both of the locking fasteners holes 116a, 116b to allow engagement with the head of the locking fastener. The hole 142 can be a blind hole, or a thru-hole. FIG. 3 depicts a thru-hole originating at the second end 106 of the body 102 extending transverse to the locking fasteners hole 116a, 116b proximate the second end 106 and opening into the upper portion of the locking fasteners hole 116a, 116b proximate to the second end 106. Likewise, the cervical plate 100 can include a thru-hole originating at the first end 104 extending transverse to the locking fasteners hole 116a, 116b proximate the first end 104 and opening into the upper portion of the locking fasteners hole 116a, 116b proximate to the first end 104.

The thru-hole depicted in FIG. 3 is sized and configured to receive a plug 144, a spring 146, and the ball 140. As further depicted in FIG. 3, the ball 140 is inserted into the thru-hole to be proximate to features of the enlarged head 134 of the locking fastener 132, the spring 146 is inserted into the thru-hole between the ball 140 and the plug 144, and the plug 144 is inserted to seal the thru-hole. The force applied by the ball 140 to the locking fastener 132 can be varied as needed by changing spring dimensions or by changing the relative position of the plug 144. In other embodiments, the hole 142 that receives the ball 140 need not be a thru-hole, and/or the hole 142 may have features or components to retain the ball 140 other than as described herein.

Figure 4:
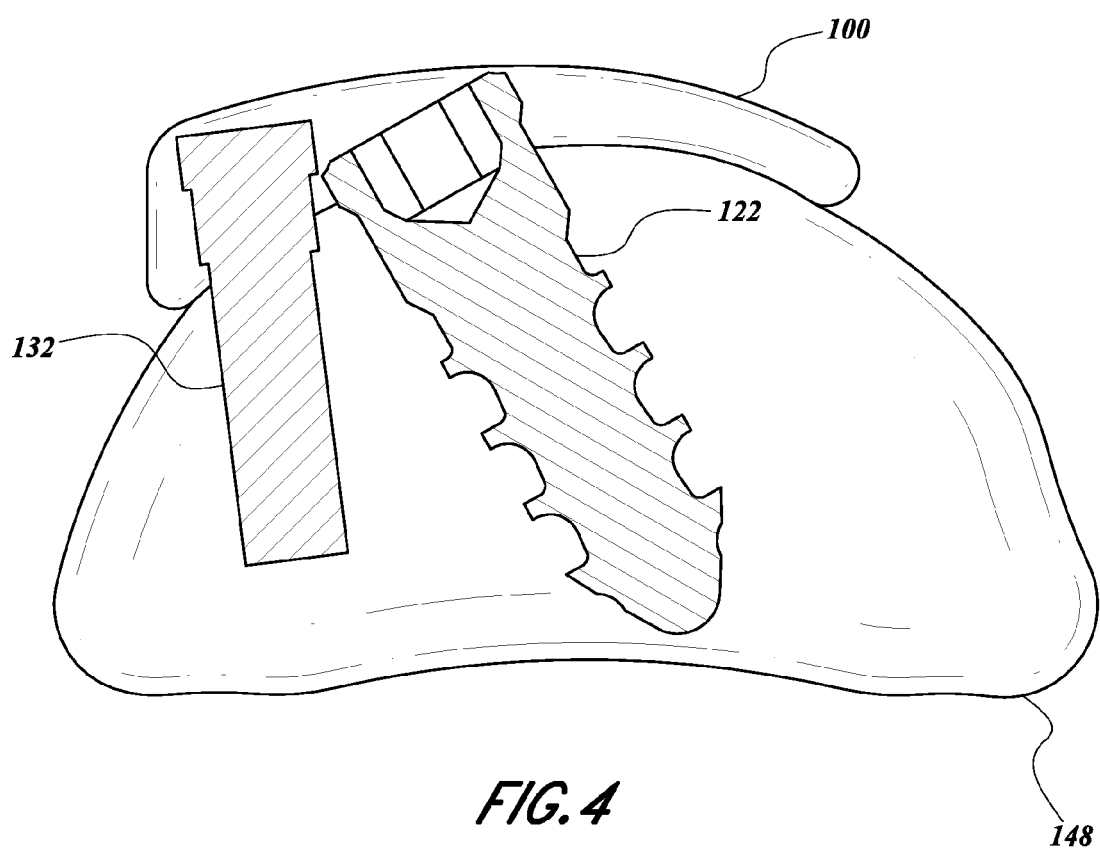
FIG. 4 is a partial cross-sectional side view showing a spinal plate affixed to a vertebral body.
Figure 6:
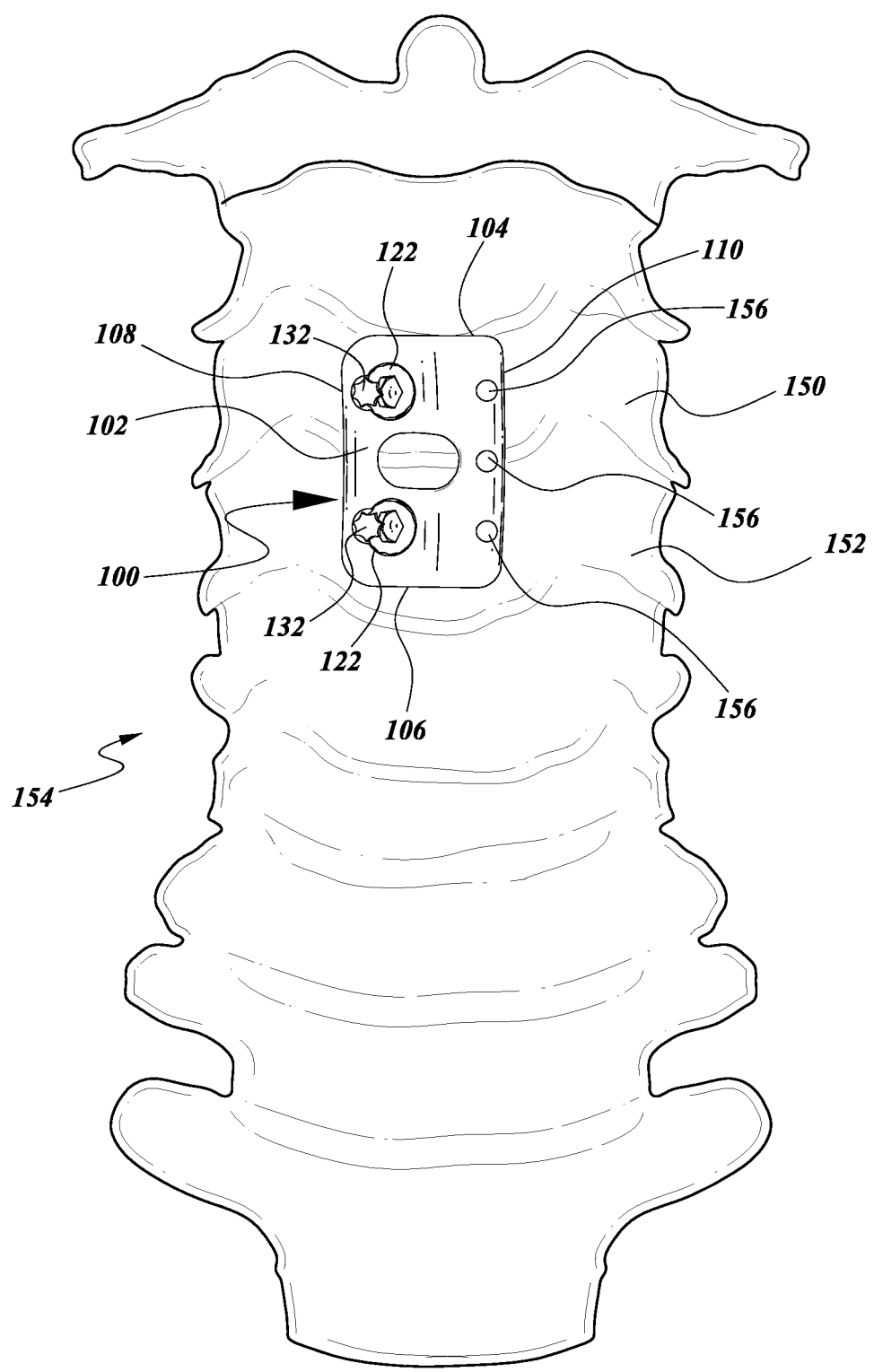
FIG. 6 illustrates one embodiment of a spinal plate attached to a plurality of vertebrae.

As shown in FIGS. 4 and 6, one example of the cervical plate 100 can be configured for use in connecting two adjacent vertebral bodies. Although the body 102 illustrated above is designed for a single level procedure connecting two vertebral bodies, additional threading and locking fasteners may be provided for insertion into additional vertebral bodies for multi-level procedures. In such embodiments, the body 102 has a length that may span three, four, five or more vertebral bodies, each of which vertebral bodies is affixed to the body 102 by at least one of the fasteners. When properly positioned along the vertebrae, both the plane passing through the longitudinal axes of threaded fasteners and the plane passing thought the longitudinal axes of the locking fasteners are approximately parallel to the vertical axis of the vertebrae to which the cervical plate 100 is attached. Thus, the threaded fastener holes 114a, 114b are vertically aligned and the locking fasteners holes 116a, 116b are also vertically aligned.

The cervical plate 100 includes features to assist in properly positioning and securing the body 102. As seen in FIG. 4, the body 102 can comprise, for example, a varying thickness so as to conform to portions of the anatomy of the cervical spine. Specifically, the generally concave lower surface 114 of the cervical plate 100 can be configured to allow the cervical plate 100 to conform to the contours of the body of a vertebra 148 when the cervical plate 100 is positioned offset from the centerline of the vertebra 148.

Figure 5:
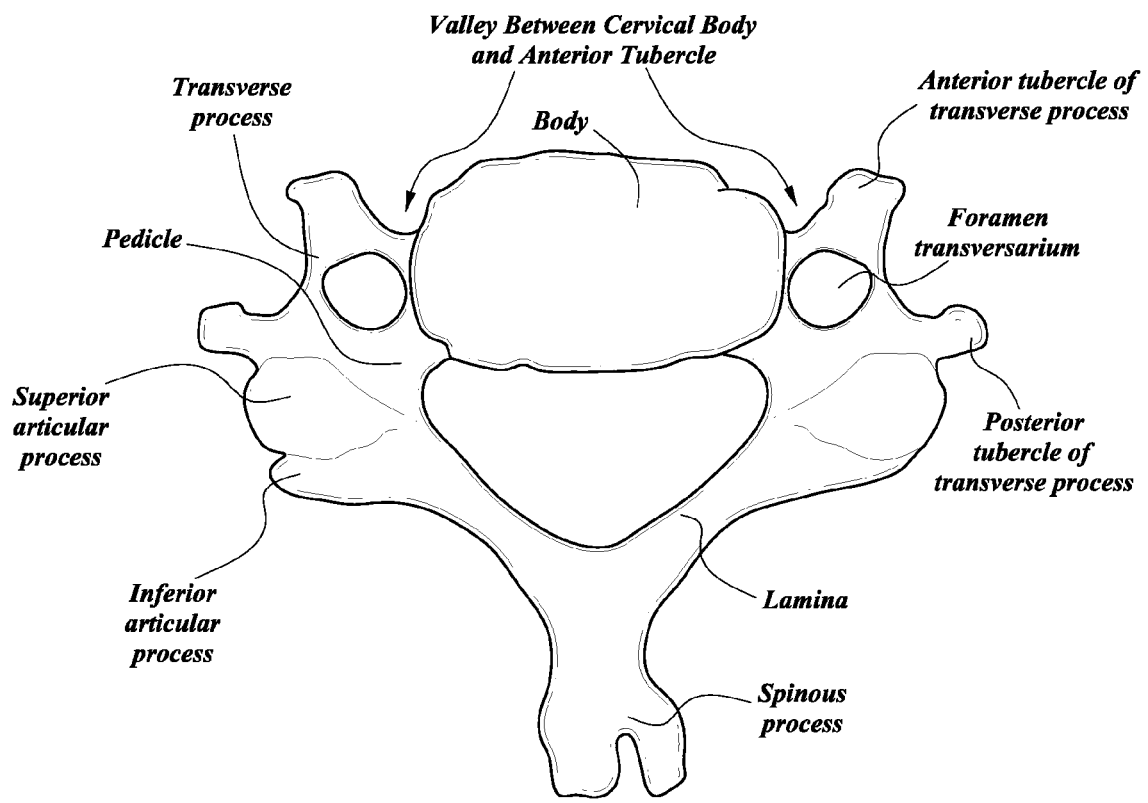
FIG. 5 illustrates certain aspects of the anatomy of a cervical vertebra.

As also seen in FIG. 4, the thickness of the cervical plate 100 varies laterally across the body 102, for example from about 3 mm to about 1 mm, with the thickest portion located in proximity to the position of the holes 114a, 114b, 116a, 116b. The thickest portion of the body 102, proximate to the thicker side 108, is configured for positioning offset from the centerline of the vertebrae in the valley between the cervical body and the cervical anterior tubercle. This, and other aspects of the anatomy of a cervical vertebra is shown in FIG. 5.

The thinnest portion of the body 102, proximate to the thinner side 110, can be configured to extend towards and over the centerline of the vertebrae to which the cervical plate 100 is attached. By enabling the offset positioning of the cervical plate 100 such that the thinner portions of the body 102 extends past the centerline of the vertebrae, the anatomical impact of the cervical plate 100 on, for example, the esophagus, is minimized. Additionally, the cervical plate 100 can be positioned so that the thick plate portion is located on the anatomical right hand side of the vertebrae, thereby providing further anatomical benefit and facilitating implantation by right-handed surgeons. More specifically, due to the anatomical leftward deviation of the esophagus in some portions of the neck, placement of the cervical plate 100 on the anatomical right hand side of the vertebrae can allow improved access to the implantation site. However, in some embodiments, the cervical plate 100 can be positioned so that the thick plate portion is located on the anatomical left hand side of the vertebrae.

The cervical plate 100 as described above may be delivered through a minimally invasive opening using retractors or other instruments known in the art. The cervical plate 100 may be implanted after delivery of cages or other implants or materials delivered into the intervertebral disc space. The cervical plate 100 is first positioned in the proper location, with the thicker side 108 positioned to anatomical right in the valley between the cervical body and the cervical anterior tubercle, and the thinner side 110 extending toward and over the centerline of the vertebrae. In such a position, the threaded fastener holes 114a, 114b are generally vertically aligned. The threaded fasteners may then be inserted each into adjacent vertebral bodies through the threaded fastener holes 114a, 114b at an oblique angle from anatomical right to anatomical left. The locking fasteners may then be delivered to secure the threaded fasteners, optionally also penetrating into the patient's vertebral bodies.

In some embodiments, the cervical plate 100 can be placed on the anatomical left side of vertebrae. In such an embodiment, the cervical plate 100 as described above may be delivered through a minimally invasive opening using retractors or other instruments known in the art. The cervical plate 100 may be implanted after delivery of cages or other implants or materials delivered into the intervertebral disc space. The cervical plate 100 is first positioned in the proper location, with the thicker side 108 positioned to anatomical left in the valley between the cervical body and the cervical anterior tubercle, and the thinner side 110 extending toward and over the centerline of the vertebrae. In such a position, the threaded fastener holes 114a, 114b are generally vertically aligned. The threaded fasteners may then be inserted each into adjacent vertebral bodies 148 through the threaded fastener holes 114a, 114b at an oblique angle from anatomical left to anatomical right. The locking fasteners 132 may then be delivered to secure the threaded fasteners 122, optionally also penetrating into the patient's vertebral bodies 148.

FIG. 6 depicts one embodiment of a cervical plate 100 affixed to the anatomical right side of a first vertebra 150 and a second vertebra 152. The first and second vertebra 150, 152 to which the cervical plate 100 is affixed can be any of the vertebrae 154. As depicted in FIG. 6, the first and second vertebrae 150, 152 to which the cervical plate 100 is affixed can be cervical vertebrae, and as specifically depicted in FIG. 6, the first vertebra 150 is the third cervical vertebra (C3) and the second vertebra 152 is the fourth cervical vertebra (C4). The body 102 illustrated in FIG. 6 differs from that of FIGS. 1 and 2 in that an additional row of vertically aligned provisional holes 156 may be provided on the thinner side 110 of the body 102. These provisional holes 156 can alternatively be located at diverse positions on the cervical plate 100, including on the thicker side 108 of the body 102, in the middle of the body 102, or on the thinner side 110 of the body 102 as depicted in FIG. 6. The provisional holes 156 in this row can be configured to receive provisional stabilizing pins. These pins can stabilize the body 102 on the vertebrae 154 during the implantation of the cervical plate 100, specifically, for example, during drilling or during screw placement. Additionally, the number, geometry, and size of the provisional holes 15 can vary depending on stabilization and other needs. As seen in FIG. 6, the cervical plate 100 is positioned on the vertebrae 154 such that the threaded fasteners holes 114a, 114b are approximately vertically aligned with each other and the locking fasteners holes 116a, 116b are approximately vertically aligned with each other. The first end 104 of the body 102 is provided towards the superior end of the patient, and the second end 106 of the body 102 is positioned toward the inferior end of the patient. In this manner, the thicker side 108 of the body 102 is positioned toward anatomical right, and the thinner side 110 of the body 102 is positioned toward anatomical left. As also seen in FIG. 6, the cervical plate 100 is positioned on the vertebrae such that one of the threaded fasteners penetrates into each of the first and second vertebrae.

Although the device is described above with respect to a use with the cervical spine, the device can be used with other portions of the spine, including, for example, the thoracic region. The device may also be used in other non-spinal orthopedic applications. The locking mechanisms described above may also be used for fasteners in other spinal devices, or other medical devices that utilize fasteners. Further, although the device is described above with respect to connecting two vertebrae, different embodiments of the body 102 can be used to connect a greater number of vertebrae, including, three, four, five, or more vertebrae.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

What is claimed is:

1. A spinal plate apparatus comprising:
   a spinal plate comprising:
   an upper surface, a lower surface, a thickness between the upper and lower surfaces, a first end and a second end defining a length therebetween configured to span two or more adjacent vertebral bodies, a first side and a second opposing side, wherein the thickness of the second side is greater than the thickness of the first side;
   at least two paired fastener holes extending through the upper and lower surfaces, wherein the at least two paired fastener holes are positioned closer to the second side than to the first side and each of the at least two paired fastener holes consists of a bone engaging fastener hole adjacent to a locking fastener hole, the bone engaging fastener hole being angled such that a bone engaging fastener passing through the hole is angled toward the first side of the spinal plate, and the locking fastener hole being configured to receive a locking fastener.

2. The spinal plate apparatus of claim 1, further comprising at least two bone engaging fasteners each configured to extend through a corresponding bone engaging fastener hole at an oblique angle extending from the second side toward the first side of the plate.

3. The spinal plate apparatus of claim 2, further comprising locking fasteners configured to be received in the locking fastener holes to secure the bone engaging fasteners to the spinal plate.

4. The spinal plate apparatus of claim 3, further comprising at least one locking feature configured to engage with the locking fasteners, wherein the locking feature is configured to secure the locking fastener.

5. The spinal plate apparatus of claim 4, wherein the locking fasteners comprise a head and a shaft, the locking feature being configured to engage with a head of at least one of the locking fasteners.

6. The spinal plate apparatus of claim 5, wherein the head of the locking fastener comprises a plurality of notches.

7. The spinal plate apparatus of claim 6, wherein the at least one locking feature comprises a spring-loaded detent ball, the detent ball being configured to engage the plurality of notches.

8. The spinal plate apparatus of claim 1, wherein a portion of the locking fastener hole is threaded.

9. The spinal plate apparatus of claim 1, wherein the bone engaging fastener hole is positioned at an acute angle relative to the locking fastener hole.

10. The spinal plate apparatus of claim 1, wherein the lower surface of the plate is concave.

11. A spinal plate apparatus comprising:
    a spinal plate having an asymmetrical configuration configured for off-center affixation to the vertebral spine, the spinal plate comprising an upper surface, a lower surface, a thickness between the upper and lower surfaces, a first side and a second opposing side, wherein the thickness of the second side is greater than the thickness of the first side;
    at least one paired fastener holes consisting of a bone engaging fastener hole adjacent to a locking fastener hole, the bone engaging fastener hole configured to receive a bone engaging fastener and the locking fastener hole configured to receive a locking fastener, the bone engaging fastener hole and locking fastener hole extending through the upper and lower surfaces, wherein the bone engaging fastener hole and locking fastener hole are positioned closer to the second side than to the first side;
    at least one bone engaging fastener configured to extend through a corresponding bone engaging fastener hole in the spinal plate at an oblique angle extending from the second side toward the first side of the plate; and
    at least one locking fastener configured to extend through a corresponding locking fastener hole in the spinal plate to secure the bone engaging fasteners to the spinal plate.

12. The spinal plate apparatus of claim 11, wherein the asymmetrical configuration comprises a variation in the thickness of the spinal plate.

13. The spinal plate apparatus of claim 12, wherein the variation in the thickness of the spinal plate corresponds to the geometry of a cervical vertebra.

14. The spinal plate apparatus of claim 11, further comprising at least one locking feature configured to engage with the locking fasteners, wherein the locking feature is configured to secure the locking fastener.

15. The spinal plate apparatus of claim 14, wherein the locking fasteners comprise a head and a shaft, the locking feature being configured to engage with a head of at least one of the locking fasteners.

16. The spinal plate apparatus of claim 15, wherein the head of the locking fastener comprises a plurality of notches.

17. The spinal plate apparatus of claim 16, wherein the at least one locking feature comprises a spring-loaded detent ball, the detent ball being configured to engage the plurality of notches.

18. A spinal plate apparatus comprising:
a spinal plate comprising:
an upper surface, a lower surface and a thickness between the upper and lower surfaces;
at least two paired fastener holes extending through the upper and lower surfaces, wherein each of the at least two paired fastener holes consists of a bone engaging fastener hole and
a locking fastener hole positioned adjacent to the bone engaging fastener hole;
at least one bone engaging fastener configured to be delivered through the bone engaging fastener hole;
at least one locking fastener configured to be delivered through the locking fastener hole to secure the bone engaging fastener to the spinal plate; and
a locking feature configured to engage with the locking fastener when the locking fastener is delivered through the locking fastener hole, wherein the locking feature is configured to secure the locking fastener and thereby secure the bone engaging fastener when the bone engaging fastener is delivered through the adjacent bone engaging fastener hole.

19. The spinal plate apparatus of claim 18, wherein the at least one bone engaging fastener comprises a threaded fastener.

20. The spinal plate apparatus of claim 18, wherein the at least one bone engaging fastener hole defines an axis through which the bone engaging fastener is delivered that is at an acute angle with an axis defined by the at least one locking fastener hole through which the locking fastener is delivered.

21. The spinal plate apparatus of claim 18, wherein the bone engaging fastener hole defines an axis through which the bone engaging fastener is delivered that is at an acute angle with the lower surface of the spinal plate, and the locking fastener hole defines an axis through which the locking fastener is delivered that is substantially perpendicular to the lower surface of the spinal plate.

22. The spinal plate apparatus of claim 18, comprising at least two bone engaging fastener holes and at least two locking fastener holes located proximate to corresponding bone engaging fastener holes.

23. The spinal plate apparatus of claim 18, wherein a portion of the locking fastener hole is threaded.

24. The spinal plate apparatus of claim 18, wherein the bone engaging fastener comprises a head and a shaft and wherein the locking fastener comprises a head and a shaft.

25. The spinal plate apparatus of claim 24, wherein the bone engaging fastener hole is positioned such that the head of the bone engaging fastener can be partially disposed between the spinal plate and the head of the locking fastener when the bone engaging fastener is inserted into the bone engaging fastener hole and the locking fastener is inserted into the locking fastener hole.

26. The spinal plate apparatus of claim 18, wherein the locking feature is configured to engage with a head of the locking fastener.

27. The spinal plate apparatus of claim 26, wherein the head of the locking fastener comprises a plurality of notches.

28. The spinal plate apparatus of claim 27, wherein the locking feature engages with the plurality of notches of the head of the locking fastener.

29. The spinal plate apparatus of claim 26, wherein the locking feature comprises a spring-loaded detent ball.

* * * * *